United States Patent [19]

Garreau et al.

[11] Patent Number: 5,132,049

[45] Date of Patent: Jul. 21, 1992

[54] SUBSTITUTED THIOPHENES, CONDUCTING POLYMERS DERIVED FROM THESE THIOPHENES, PROCESS FOR OBTAINING THEM AND DEVICES CONTAINING THESE POLYMERS

[75] Inventors: Robert Garreau, Sarcelles; Jean Roncali, Les Lilas; Marc Lemaire, Nanterre; Hafsa Korri, Paris; Francis Garnier, Champigny, all of France; Etienne Hannecart, Tervuren, Belgium

[73] Assignee: Solvay & Cie (Société Anonyme), Brussels, Belgium

[21] Appl. No.: 444,885

[22] Filed: Dec. 4, 1989

[30] Foreign Application Priority Data

Dec. 16, 1988 [FR] France ................. 88 16784

[51] Int. Cl.$^5$ .................. H01B 1/12; C08F 28/06
[52] U.S. Cl. ................... 252/500; 252/518; 526/256; 528/390
[58] Field of Search ............ 252/500, 518; 526/256; 528/390

[56] References Cited

U.S. PATENT DOCUMENTS

| | | | |
|---|---|---|---|
| 4,501,686 | 2/1985 | Hotta et al. | 252/500 |
| 4,691,005 | 9/1987 | Sato et al. | 204/59 R |
| 4,892,678 | 1/1990 | Tanaka et al. | 252/500 |
| 4,909,959 | 3/1990 | Lemaire et al. | 252/500 |
| 4,992,559 | 2/1991 | Kathirgamanathan | 526/256 |

FOREIGN PATENT DOCUMENTS

| | | |
|---|---|---|
| 0203438 | 12/1986 | European Pat. Off. |
| 0240063 | 10/1987 | European Pat. Off. |
| 0253594 | 1/1988 | European Pat. Off. |
| 2527843 | 12/1983 | France. |
| 88/00954 | 2/1988 | World Int. Prop. O. ......... 528/256 |

Primary Examiner—Paul Lieberman
Assistant Examiner—Linda D. Skaling
Attorney, Agent, or Firm—Spencer, Frank & Schneider

[57] ABSTRACT

Substituted thiophenes of the general formula:

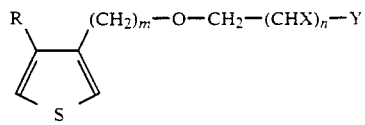

in which:
R represents a hydrogen atom, a halogen atom or an aliphatic group containing from 1 to 4 carbon atoms,
X represents a hydrogen atom or a fluorine atom.
Y represents an at least partially fluorinated aliphatic or aromatic group,
m represents an integer equal to or greater than 2, and
n represents an integer such that $0 \leq n \leq 7$.

The invention also relates to the electrically conducting polymers containing recurring units derived from monomers chosen from the substituted thiophenes.

3 Claims, 4 Drawing Sheets

SUBSTITUTED THIOPHENES, CONDUCTING POLYMERS DERIVED FROM THESE THIOPHENES, PROCESS FOR OBTAINING THEM AND DEVICES CONTAINING THESE POLYMERS

FIELD OF THE INVENTION

The present invention relates to thiophenes substituted by a group containing an ether function and an at least partially fluorinated aliphatic or aromatic radical. The invention also relates to electrically conducting polymers containing recurring units derived from these substituted thiophenes and to a process for the production of the substituted thiophenes and a process for the production of the polymers and the electrically conducting devices containing these polymers.

TECHNOLOGY REVIEW

Electrically conducting polymers derived from monomers of the general formula:

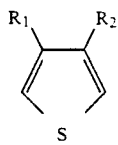

are known and have been described, in particular, in European Patent Application EP 0,253,594 (Cookson Group); in this general formula $R_1$ may represent, inter alia, an aryloxyalkyl group or a group of the formula $-(CH_2)_n-O-(CH_2CH_2)_p-O-R_4$ in which $R_4$ represents an alkyl group containing from 1 to 6 carbon atoms and $R_2$ represents a hydrogen atom, a halogen atom or an amino group.

Likewise, electrically conducting polymers derived from monomers of the general formula:

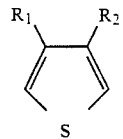

in which $R_1$ may represent, inter alia, an alkoxy, aryloxy, alkoxyalkyl or alkyl group substituted by an epoxy, halogen or carboxylic acid group and $R_2$ represents a hydrogen atom or a methyl radical have been described in European Patent Application EP 203,438 (Allied Corporation).

However, certain electrical applications, such as the production of devices (display screens, commutators, memory elements . . . ) based on electrochromism (involving a modification of the light absorption or transmission properties of the material used, induced by a variation in the external voltage applied), electrodes of rechargeable batteries, photovoltaic cells, electrochemical cells, electromagnetic wave absorption devices, etc. demand conducting polymers with special properties.

These special properties are, in particular, the most complete possible electrochemical reversibility and the highest possible stability of the oxidation/reduction cycle between the oxidized and reduced forms of the polymer/doping agent system and also a significant variation in the spectral characteristics obtained with a very small variation in potential, a good electrical conductivity and significant absorptions in the range of near infrared and high-frequency radiation.

SUMMARY OF THE INVENTION

The present invention aims to provide a new family of substituted thiophenes enabling, in particular, electrically conducting polymers to be obtained which have the abovementioned special properties to a high degree.

DETAILED DESCRIPTION OF THE INVENTION

Figure 1:
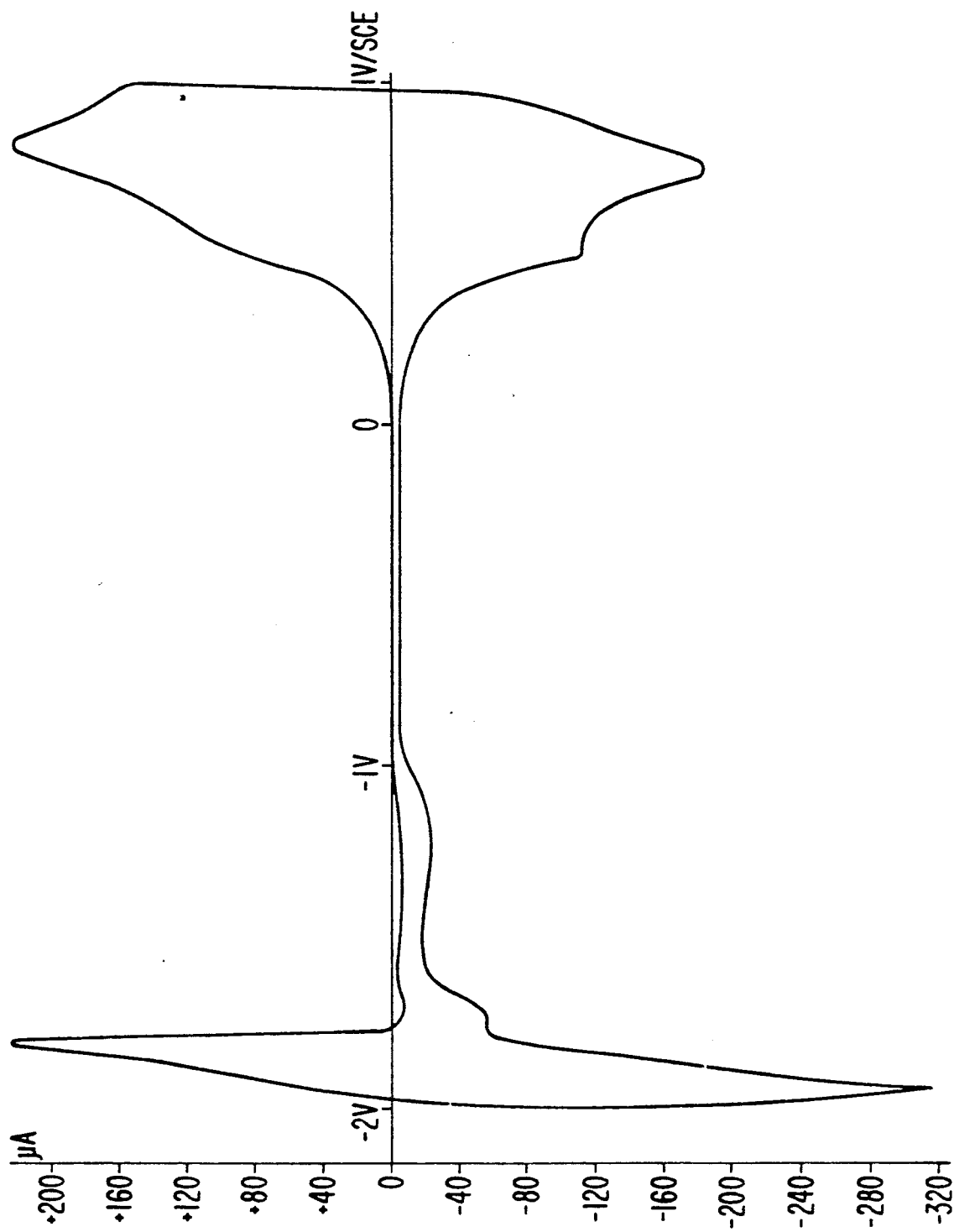
FIG. 1 illustrates electrochemical properties of a polymer according to the invention shown by a voltammogram.
Figure 2:
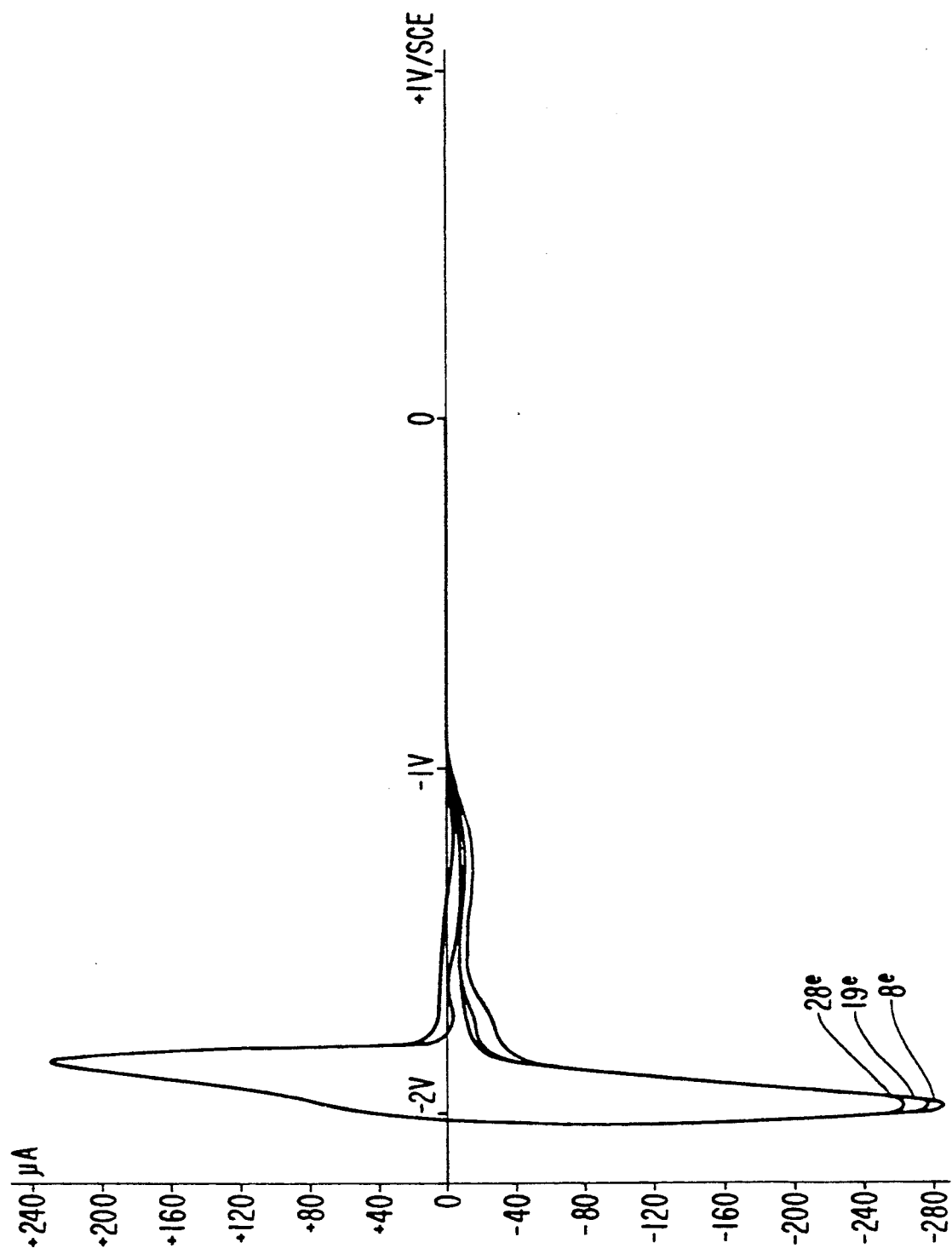
FIGS. 2 and 3 illustrate the effect of redox cycling on the same polymer.
Figure 3:
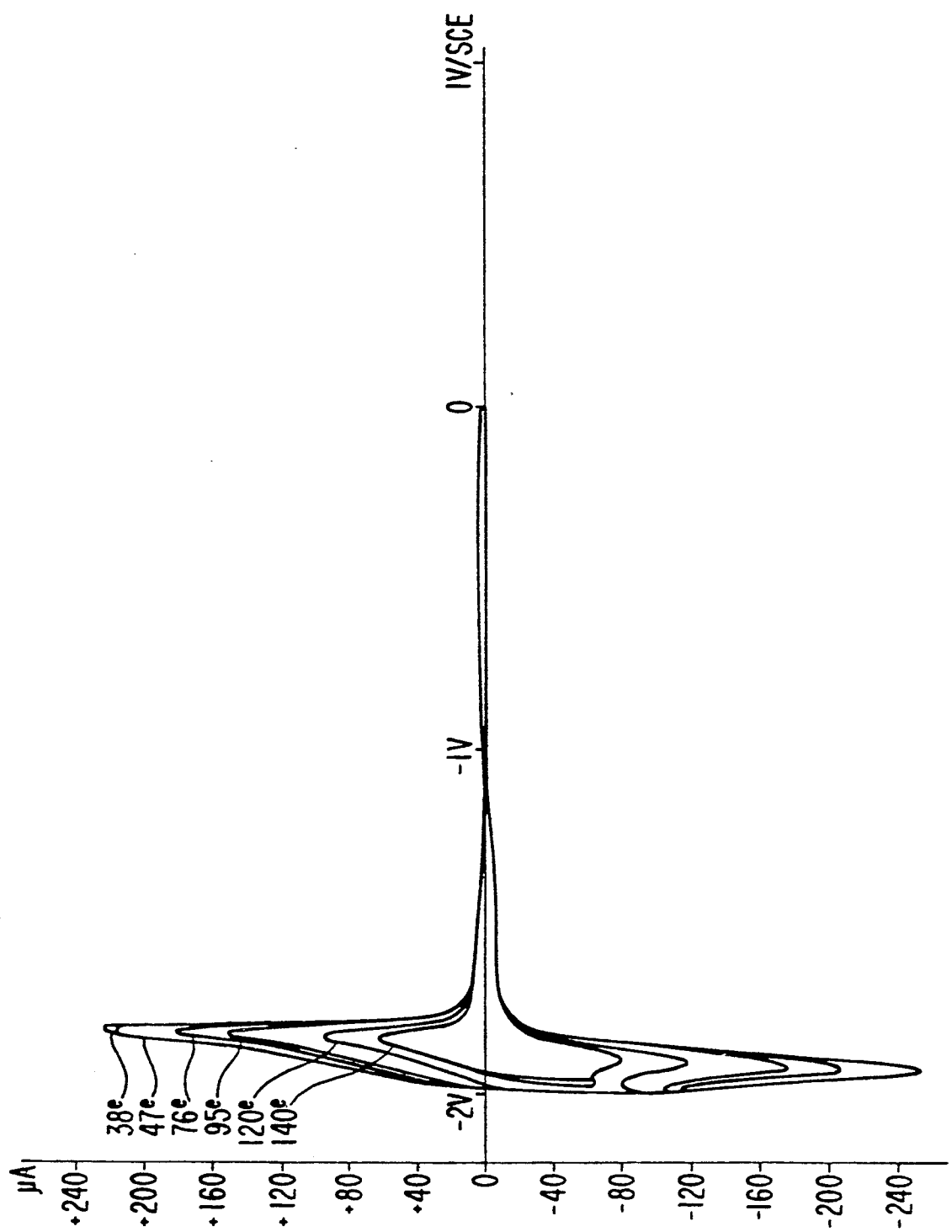
Figure 4:
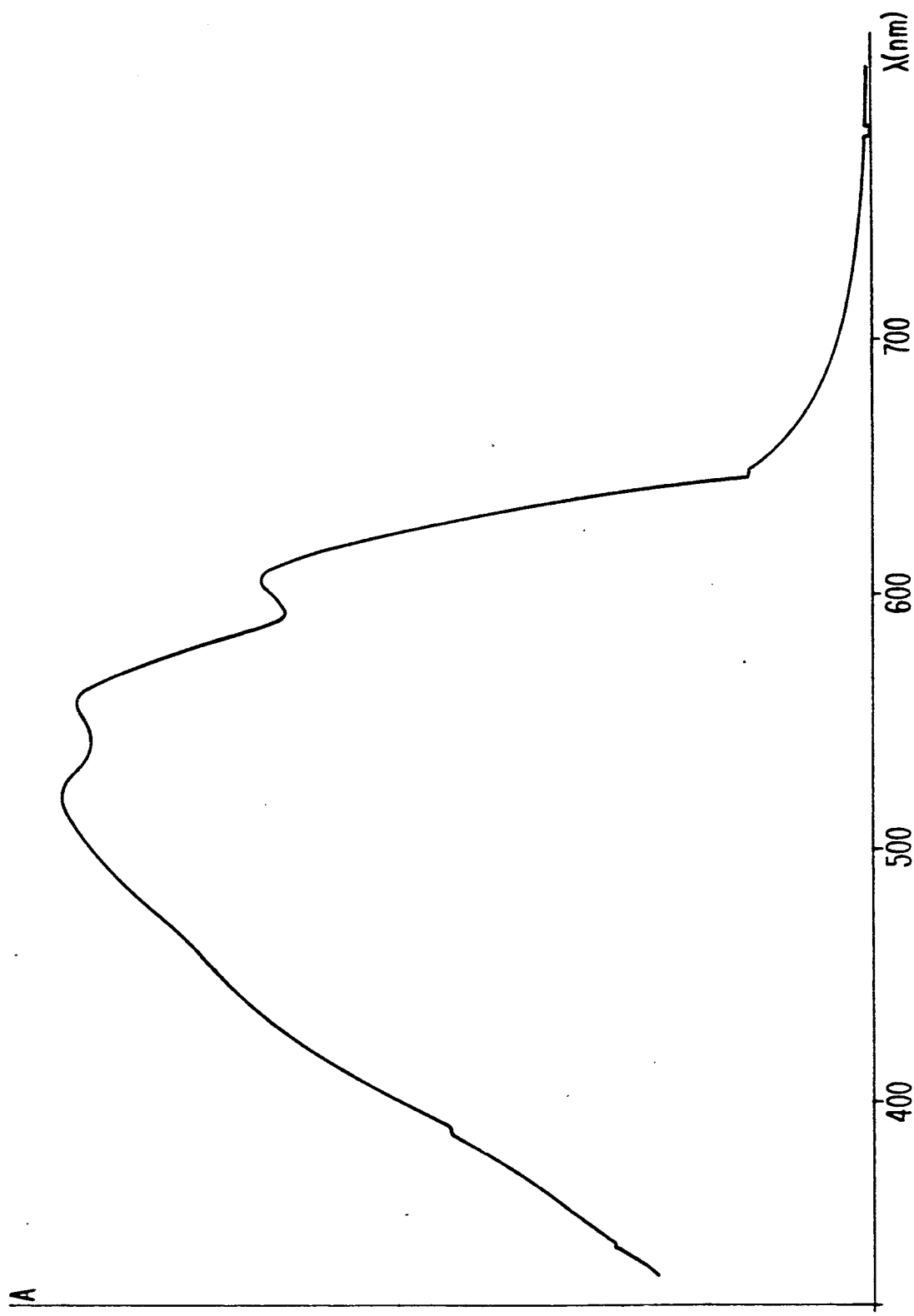
FIG. 4 illustrates the absorption spectrum of a dedoped polymer.

To this end, the invention relates to monomers derived from substituted thiophenes of the general formula:

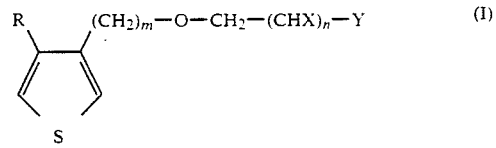

in which:

R represents a hydrogen atom, a halogen atom or an aliphatic group containing from 1 to 4 carbon atoms, X represents a hydrogen atom or a fluorine atom, Y represents an at least partially fluorinated aliphatic or aromatic group, m represents an integer equal to or greater than 2, and n represents an integer such that $0 \leq n \leq 7$.

Usually:

R represents a hydrogen atom,

X represents a hydrogen atom or a fluorine atom,

Y represents:

a phenyl radical substituted at least by a fluorine atom, by a $-CH_3$ group, a $-CH_2F$ group or a $CHF_2$ group, or an aliphatic group of the general formula $-(CF_2)_p-CF_3$ in which p represents an integer such that $0 \leq p \leq 16$, m represents an integer equal to or greater than 2, and n represents an integer such that $0 \leq n \leq 7$.

In general:

R represents a hydrogen atom,

X represents a hydrogen atom,

Y represents:

a phenyl radical substituted by a fluorine atom, by a $-CF_3$ group or entirely substituted by fluorine atoms, or an aliphatic group of the general formula $-(CF_2)_p-CF_3$, in which p represents an integer such that $0 \leq p \leq 12$, m represents an integer equal to 2 or 3, and n represents an integer such that $0 \leq n \leq 2$.

Preferably:

R represents a hydrogen atom,

X represents a hydrogen atom,

Y represents:

a phenyl radical substituted in the para-position by a fluorine atom, in the para-position by a —CF₃ group or entirely substituted by fluorine atoms, or an aliphatic group of the general formula —(CF$_2$)$_p$—CF$_3$ in which p represents an integer such that $0 \leq p \leq 8$, m is equal to 2, and n represents an integer equal to 0 or 1.

Particularly preferably:

R represents a hydrogen atom,

X represents a hydrogen atom,

Y represents a phenyl radical substituted in the para-position by a fluorine atom, m is equal to 2, and n is equal to 0.

This product corresponds to 4-fluorobenzyl-2-(3-thienyl)ethyl ether.

The substituted thiophenes according to the invention can be synthesized according to known methods, for example by reacting compounds of the general formulae:

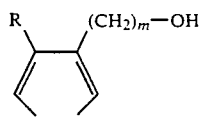

(II)

with Q—CH$_2$—(CHX)$_n$—Y    (III)

in which R, X, Y, m and n are as defined above and Q represents a halogen atom such as, in particular, a bromine atom or a chlorine atom and preferably a bromine atom. Good results have been obtained by reacting 2-(3'-thienyl)-ethanol or 3-(3'-thienyl)-1'-propanol with the appropriate alkyl halide, oxyalkyl halide, phenyl halide or benzyl halide. Thus, for example, 4-fluorobenzyl 2-(3-thienyl)ethyl ether is prepared by reacting 2-(3'-thienyl)-ethanol with 1-bromomethyl-4-fluorobenzene in tetrahydrofuran in the presence of sodium hydride.

The temperature at which this reaction is carried out is generally between 5° and 50° C. and preferably between 10° and 30° C.

The pressure at which this reaction is carried out is generally between 1 and 4 bars; preferably the reaction is carried out at atmospheric pressure.

The reaction is preferably carried out under the atmosphere of an inert gas, such as, in particular, argon, and in the presence of a solvent, such as, in particular, tetrahydrofuran, and may be carried out in any reactor or equipment enabling the abovementioned conditions to be met.

The polymers containing recurring units derived from substituted thiophene according to the invention form another subject of the invention.

To this end, the invention relates to polymers containing recurring units of the general formula:

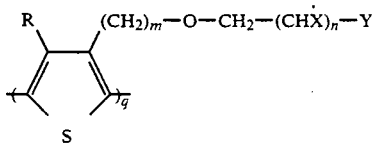

(IV)

in which:

q represents an integer,

R represents a hydrogen atom, a halogen atom or an aliphatic group containing from 1 to 4 carbon atoms, X represents a hydrogen atom or a fluorine atom, Y represents an at least partially fluorinated aliphatic or aromatic group, m represents an integer equal to or greater than 2, and n represents an integer such that $0 \leq n \leq 7$.

Usually:

q represents an integer of between 2 and 5,000,

R represents a hydrogen atom,

X represents a hydrogen atom or a fluorine atom,

Y represents:

a phenyl radical substituted at least by a fluorine atom or by a —CF₃ group, a —CH₂F group or a CHF₂ group, or an aliphatic group of the general formula —(CF$_2$)$_p$—CF$_3$ in which p represents an integer such that $0 \leq p \leq 16$, m represents an integer equal to or greater than 2, and n represents an integer such that $0 \leq n \leq 7$.

In general:

q represents an integer of between 2 and 3,000,

R represents a hydrogen atom,

X represents a hydrogen atom,

Y represents:

a phenyl radical substituted by a fluorine atom, by a —CF₃ group or entirely substituted by fluorine atoms, or an aliphatic group of the general formula —(CF$_2$)$_p$—CF$_3$, in which p represents an integer such that $0 \leq p \leq 12$, m represents an integer equal to 2 or 3, and n represents an integer such that $0 \leq n \leq 2$.

Preferably:

q represents an integer of between 2 and 1,000,

R represents a hydrogen atom,

X represents a hydrogen atom,

Y represents:

a phenyl radical substituted in the para-position by a fluorine atom, in the para-position by a —CF₃ group or entirely substituted by fluorine atoms, or an aliphatic group of the general formula —(CF$_2$)$_p$—CF$_3$, in which p represents an integer such that $0 \leq p \leq 8$, m is equal to 2, and n represents an integer equal to 0 or 1.

Particularly preferably:

q represents an integer of between 2 and 500,

R represents a hydrogen atom,

X represents a hydrogen atom,

Y represents a phenyl radical substituted in the para-position by a fluorine atom, m is equal to 2, and n is equal to 0.

This product corresponds to the polymer of 4-fluorobenzyl 2-(3-thienyl)ethyl ether.

The electrically conducting polymers containing a polymer according to the invention and a doping agent form another subject of the invention. The doping agent can be an anion or a cation, as defined below.

The preparation of the electrically conducting polymers according to the invention can be effected by a chemical route, for example in the presence of oxidizing agents, or by an electrochemical route. The preferred procedure is by electrochemical polymerization, generally in an electrolysis cell, by anodic oxidation of the monomer in a polar solvent and in the presence of appropriate electrolytes in accordance with conventional techniques such as are described, in particular, in French Patent Application FR-A-2,527,843.

According to these techniques, the monomer concentration is generally between $10^{-3}$ and 1 mole per litre of solvent.

The temperature at which the preparation of the polymers is carried out is generally between 0° and 50° C. and preferably between 5° and 40° C.

The pressure at which the preparation of the polymers is carried out is generally close to atmospheric pressure and preferably is equal to atmospheric pressure.

Solvents used are preferably polar solvents which possess dissolving properties vis à vis both the monomer and the electrolyte chosen and are stable in the range of potentials applied. Examples of solvents which can be used are acetonitrile, tetrahydrofuran, methylene chloride, nitrobenzene and propylene carbonate.

The electrolytes are generally chosen from the conducting salts of the formula $C^+A^-$, in which $C^+$ is a cation and in which $A^-$ is an anion.

The cation $C^+$ is preferably chosen from the alkali metal ions and the ions $R_4N^+$ and $R_4P^+$ (R being an alkyl radical, such as the ethyl and butyl radicals, for example).

The anion $A^-$ is preferably chosen from the ions $ClO_4^-$, $AsF_6^-$, $SbF_6^-$, $SO_4^{2-}$, $C_6H_5SO_3^-$, $BF_4^-$, $PF_6^-$ and $CF_3SO_3^-$.

Typical electrolytes are, for example, the fluorophosphates, such as tetrabutylammonium hexafluorophosphate, the fluoborates, such as tetraethylammonium tetrafluoborate, and the perchlorates, such as lithium perchlorate and tetrabutylammonium perchlorate.

The concentration of electrolyte is generally between $10^{-3}$ and 1 mole per liter of solvent.

The electrochemical cell in which the polymerization of the monomers according to the invention can be carried out can operate under potentiostatic or galvanostatic conditions.

In the first case (potentiostatic control), the cell comprises, in addition to the source of external current, three electrodes, one electrode of which is a reference electrode for monitoring the potential.

In the course of the electrolysis, a layer of polymer is deposited on the conducting element used as the anode in the electrolysis cell. This anode can be made of a noble metal, such as gold or platinum, or of another metal, such as copper, which is gold-plated or platinum-plated, titanium or nickel or of a conducting glass, (tin oxide, indium/tin oxides). After the electrolysis there is thus, in fact, an electrode made up of a conducting body covered by a film of polymer which adheres thereto and which contains a certain proportion of the anion originating from the electrolyte. The polymer and the anion thus form a charge transfer complex. The chemical composition of the polymer film can be represented by the empirical formula $(M^+Ay^-)_q$ where $M^+$ represents the monomer, $A^-$ represents the anion or counterion, y represents the proportion of anion in the polymer expressed per monomer unit (that is to say the level of doping), which, in the case of the polymers of the invention, may reach a value of 0.5, and q represents the degree of polymerization, which is generally difficult to determine easily, given the insoluble nature of the polymer.

Since the electrochemical polymerization of the monomer takes place at the anode of the electrolysis cell, it is not possible directly to obtain an electrode covered by a polymer doped by cations.

In order to obtain such a cathode, the anode previously obtained can be used and subjected to a double reduction. A first electrochemical reduction is possible directly after the polymerization by leaving the anode in the electrolysis cell and causing discharge of the cell. This discharge causes the extraction of the anions "doping" the polymer. A second reduction can then be carried out under an inert atmosphere, either by a chemical route or by an electrochemical route. The chemical route consists in immersing the polymer in a solution containing the desired cations. Thus, in order to obtain a polymer "doped" for example by $Li^+$, $Na^+$ or $K^+$ cations (doping of the "n" type, to which the polymers according to the invention are particular amenable), it is possible to use, for example, a solution of naphthalene-lithium, naphthalene-sodium or naphthalenepotassium in tetrahydrofuran. The electrochemical route usually consists in placing the electrode as the cathode in an electrolysis cell containing the desired cations in solution. The cations can be, for example alkali metal ions, such as those mentioned above, preferably $Li^+$ or $K^+$ cations, or complex ions, such as $(Bu)_4N^+$ or $(Et)_4N^+$ resulting from an electrolyte (preferably $LiClO_4$, $KPF_8$, resulting from an electrolyte (preferably $LiClO_4$, $KPF_6$, $(Bu)_4NClO_4$ and $(Et)_4NClO_4$) in solution in a solvent such as acetonitrile, tetrahydrofuran or propylene carbonate. The electrolyte concentration in the solution is generally between $10^{-3}$ and 1 mole per 1 liter of solvent.

The conducting polymers according to the invention have an entirely surprising spectrum of properties, which are in the main:

an exceptional reversibility and stability of the oxidation-reduction cycle between their oxidized and reduced forms; thus, in particular, for the preferred polymer amongst these polymers, the stability of the oxidation-reduction cycle is such that the polymer can be subjected to up to $0.5 \times 10^7$ cycles while still maintaining 90% of the initial charge;

a significant variation in the spectral characteristics obtained with a small variation in potential, which makes the use of these polymers as electrochromic material advantageous and economical;

a good electrical conductivity, generally of between 1 and $2.10^2$ S.cm$^{-1}$;

significant absorptions in the range of near infrared and high-frequency radiation.

These surprising properties of the conducting polymers according to the invention make them particularly suitable for use for the production of electrically conducting devices for which the operating principle is based on these properties and which are likewise a subject of the present invention.

The following may be mentioned by way of non-limiting examples of electrically conducting devices containing conducting polymers derived from substituted aromatic heterocyclic monomers according to the invention:

electrochemical devices for storing energy, such as batteries of accumulators and rechargeable or non-rechargeable cells, in which the anodes (or the cathodes) are constituted by electrodes coated with films of the said polymers doped by anions (or cations);

electrochronic devices based on the modification of the optical spectrum of the said polymers according to their oxidation state, which manifests itself during the oxidation and reduction cycles of the polymer films deposited on the anodes (or the cathodes) of these devices during charging and discharging; examples of such electrochronic devices which may be mentioned are display screens, opto-electronic devices, optical memories and commutators and electromagnetic wave absorption devices.

The invention is illustrated by the following examples.

EXAMPLE 1

The following are introduced successively into a 1 l three-necked flask placed under argon: 120 ml of tetrahydrofuran dried over sodium, 120 mmol of sodium hydride as a 60% suspension in mineral oil and then, in the course of 10 minutes, a solution 100 mmol of 2-(3'-thienyl)-ethanol in 60 ml of tetrahydrofuran.

The suspension is stirred at 20° C. under an argon atmosphere for 30 min.

A solution of 130 mmol of 1-bromoethyl-4-fluorobenzene in 120 ml of tetrahydrofuran is then added in the course of 30 min.

The suspension is refluxed under an argon atmosphere for 4 hours.

The suspension which has cooled to ambient temperature is treated with 120 ml of ether and 100 ml of water.

The organic phase is decanted off, then washed three times with 100 ml of water, then dried over magnesium sulphate and evaporated to dryness under vacuum.

The crude product is purified by chromatography ($SiO_2$/heptane/AcOEt) and then distilled under vacuum.

The yield of 4-fluorobenzyl 2-(3'-thienyl)ethyl ether is 75%, calculated in mole per cent.

EXAMPLE 2

The synthesis of the polymer is carried out in a single—compartment, thermostatically-controlled cell containing:

$2.10^{-1}$ mole of monomer prepared as in Example 1,
$3.10^{-2}$ mole of tetrabutylammonium hexafluorophosphate (supplied by Fluka,) and
25 ml of distilled nitrobenzene.

The polymer deposits are produced at 5° C., under an argon atmosphere, after degassing the solution by bubbling argon through it. For the electrochemical characteristics, the polymer is deposited on a solid platinum electrode with a polished surface area of 0.7 cm$^2$. The quantity of charges used is 100 mC/cm$^2$ and the current density is equal to 2 mA/cm$^2$, which leads to a polymer deposit about 0.45 μ thick. The cathode consists of a platinum wire and the reference electrode is a saturated calomel electrode.

The electrical conductivity of the polymer thus obtained is of the order of 5 S.cm$^{-1}$.

The absorption spectrum of the dedoped polymer is shown in Figure IV. The absorption is significant between 450 and 600 nm and very low beyond 600 nm. The wavelength (λ) on the abscissa is measured in nanometres (nm) and the absorbence (A) is given as the ordinate (arbitrary unit).

The electrochemical properties of the polymers were measured from the cyclic voltammogram recorded by means of a model 173 PAR potentiostat and from the intensity peaks recorded. Figure I shows a voltammogram obtained using a scanning speed of 100 mV/s in 0.1 mole of tetraethylammonium perchlorate dissolved in $CH_3CN$, the unit of the abscissa is the volt (V) and the unit of the ordinate is the microampere (μA).

The $Ip_a/Ip_c$ ratios between the oxidation current intensity ($Ip_a$) and the reduction current intensity ($Ip_c$) (for the system p) are about 1.

The doping "p" of the polymer is highly reversible. The charge exchanged after 10$^6$ cycles is still 95%.

The experiment is carried out with the aid of potential pulses located between 0 and 0.7 volt relative to the silver wire and 50 ms in duration, under conditions which enable the optical contrast to be seen (film thickness: 0.10 μ).

The redox cycling is carried out in an electrolytic medium consisting of propylene carbonate containing $5.10^{-1}$ mole of anhydrous lithium perchlorate.

The tests to determine the doping "n" were carried out in propylene carbonate containing 0.1 mole of tetraethylammonium perchlorate.

When the procedure is not in accordance with the special conditions (degassing with argon and solvents dried over $P_2O_5$) to prevent the oxidation of the doped polymers n formed, the succession of cycles indicated in Figures II and III is obtained. These were carried out using a scanning speed of 100 mV/s in 0.1 mole of tetraethylammonium perchlorate dissolved in $CH_3CN$; the figures (8th, 19th, 28th for Figure II and 38th, ..., 140th for Figure III) represent the number of cycles carried out. The unit for the abscissa is the volt and the unit for the ordinate is the microampere.

We claim:

1. Thiophenes of the general formula:

$$\underset{S}{\underset{\diagdown}{\overset{R}{\diagup}}\underset{\diagup}{\overset{(CH_2)_m-O-CH_2-(CHX)_n-Y}{\diagdown}}}_q \qquad (IV)$$

in which:
q represents an integer such that $2 \leq q \leq 5000$
R represents a hydrogen atom, a halogen atom or an aliphatic group containing from 1 to 4 carbon atoms,
X represents a hydrogen atom or a fluorine atom,
Y represents an at least partially fluorinated aliphatic or aromatic group,
m represents an integer equal to or greater than 2, and
n represents an integer such that $0 \leq n \leq 7$.

2. Thiophene according to claim 1, wherein said thiophene is the polymer of 4-fluorobenzyl 2-(3-thienyl)-ethyl ether.

3. An electrically conducting polymer, containing:
a) a doping agent comprising an anion or a cation and
b) thiophenes of the formula:

$$\underset{S}{\underset{\diagdown}{\overset{R}{\diagup}}\underset{\diagup}{\overset{(CH_2)_m-O-CH_2-(CHX)_n-Y}{\diagdown}}}_q \qquad (IV)$$

in which:
q represents an integer such that $2 \leq q \leq 5000$,
R represents a hydrogen atom, a halogen atom or an aliphatic group containing from 1 to 4 carbon atoms,
X represents a hydrogen atom or a fluorine atom,
Y represents an at least partially fluorinated aliphatic or aromatic group,
m represents an integer equal to or greater than 2, and
n represents an integer such that $0 \leq n \leq 7$, said doping agent present in said polymer up to a value of about 0.5 per monomer unit.

* * * * *